US012440179B2

(12) United States Patent
Schmidt et al.

(10) Patent No.: US 12,440,179 B2
(45) Date of Patent: Oct. 14, 2025

(54) METHOD FOR OPERATION OF A DOCKING ARRANGEMENT AND DOCKING ARRANGEMENT

(71) Applicant: Siemens Healthineers AG, Forchheim (DE)

(72) Inventors: Verena Schmidt, Erbendorf (DE); Andreas Deinlein, Bayreuth (DE); Matthias Müller, Bamberg (DE); Günther Gambke, Weidenberg (DE); Rolf Schmidt, Bayern (DE); Josef Zeidler, Marktredwitz (DE); Patrik Schwingenschlögl, Fürth (DE); Thorsten Gecks, Weidenberg (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/813,398

(22) Filed: Aug. 23, 2024

(65) Prior Publication Data

US 2025/0064412 A1 Feb. 27, 2025

(30) Foreign Application Priority Data

Aug. 24, 2023 (DE) ..................... 10 2023 208 129.6

(51) Int. Cl.
*A61B 6/04* (2006.01)

(52) U.S. Cl.
CPC .................................. *A61B 6/0407* (2013.01)

(58) Field of Classification Search
CPC ....... A61B 6/0407; A61B 6/547; A61B 5/704; A61G 13/0018; A61G 13/10; A61G 2203/80

(Continued)

(56) References Cited

U.S. PATENT DOCUMENTS 6,640,364 B1 * 11/2003 Josephson .............. A61B 5/704
5/601
6,776,527 B1 * 8/2004 Tybinkowski ........... A61B 6/04
378/209

(Continued)

FOREIGN PATENT DOCUMENTS

CN 109414240 A 3/2019
CN 111469950 A 7/2020

(Continued)

OTHER PUBLICATIONS

Machine Translation of DE-202020104652-U1.*

(Continued)

*Primary Examiner* — David R Hare
(74) *Attorney, Agent, or Firm* — Banner & Witcoff Ltd.

(57) ABSTRACT

In a method for operation of a docking arrangement, position information is determined that describes a position of the patient table, including detecting, sensor data corresponding to: the position of the patient table relative to the docking arrangement, and/or to an environment feature describing a movement trajectory to the docking arrangement. The method may further include performing, in response to a switchover condition indicative of a handover situation and a purely manual operation of the patient table by an operator, a switch into an assistance operating mode of the docking arrangement. In the assistance operating mode, at least one guidance measure may be determined for the patient table and a functional component of the patient table may be controlled to assist the operator.

17 Claims, 6 Drawing Sheets

(58) Field of Classification Search
USPC ........................................................... 5/601
See application file for complete search history.

(56) References Cited

U.S. PATENT DOCUMENTS

| | | | | |
|---|---|---|---|---|
| 6,973,689 | B2 * | 12/2005 | Lenting ................ | A61B 6/0487<br>5/601 |
| 12,239,468 | B2 * | 3/2025 | Neuber .................. | A61B 5/055 |
| 2014/0331406 | A1 * | 11/2014 | Haider ................. | A61G 13/128<br>701/23 |
| 2018/0329422 | A1 * | 11/2018 | Biber ................... | G05D 1/0088 |
| 2019/0209104 | A1 | 7/2019 | Dirauf et al. | |
| 2021/0007915 | A1 * | 1/2021 | DeLuca ............... | A61G 1/0287 |
| 2022/0047218 | A1 * | 2/2022 | Neuber .................. | A61B 5/704 |

FOREIGN PATENT DOCUMENTS

| | | | | |
|---|---|---|---|---|
| CN | 113520469 A | 10/2021 | | |
| CN | 115633052 A | 1/2023 | | |
| CN | 115998532 A | 4/2023 | | |
| DE | 202016007430 U1 | 1/2017 | | |
| DE | 202020104652 U1 * | 9/2020 | ............... | A61B 5/70 |

OTHER PUBLICATIONS

May 18, 2024 (DE) Office Action—App. 102023208129.6 (w/English Translation).

Sep. 3, 2024 (DE) Decision to Grant—App. 10202310812936 (w/English Translation).

* cited by examiner

METHOD FOR OPERATION OF A DOCKING ARRANGEMENT AND DOCKING ARRANGEMENT

CROSS REFERENCE TO RELATED APPLICATIONS

This patent application claims priority to German Patent Application No. 10 2023 208 129.6, filed Aug. 24, 2023, which is incorporated herein by reference in its entirety.

BACKGROUND

Field

The disclosure relates to a method for operation of a docking arrangement consisting of a docking facility for a patient table, a controller and the patient table which, by docking of the patient table onto the docking facility, is able to be connected to a medical engineering facility to which the docking facility belongs. In addition, the disclosure relates to a docking arrangement.

Related Art

In many cases it is possible to transport patients, in particular those who must be lying down, by means of a patient table, which has a patient couch for supporting the patient (patient support plate), to medical engineering facilities, for example imaging facilities where, by means of a docking facility, with appropriate positioning of the patient table, the patient couch can be moved from the patient table to fit exactly into a guide or other holder of the medical engineering facility, thus enabling it to be handed over into the medical engineering facility. Here a docking connection can also be established between the patient table and the docking facility. The docking facility may provide for the docking of the patient table in a docking position in such a way that a precise-fit transition between the patient table and the medical engineering facility can be provided for the patient couch or can be established for it. Magnetic resonance facilities are an example of such medical engineering facilities, in which the patient on the patient couch must be moved into the mostly cylindrical longitudinal patient tunnel and positioned there according to the examination region to be recorded. After the measures on the patient in the medical engineering facility, in particular the imaging, have been concluded, the patient couch can be moved back onto the still docked patient table and the docking connection, where one is provided, released again.

Patient tables are usually designed in such a way that they can be moved manually by an operator, for example a medical technician or a care assistant. To this end the patient table can for example have wheels and handling means, for example appropriate handles.

Difficulties occur, in particular if the operator has little experience, when the docking facility of the medical engineering facility has to be hit exactly, i.e. the docking position is to be reached as precisely as possible. The result in such cases can be that a number of approaches are needed in order to allow docking. Over and above this a patient couch can in many cases also be drawn in or a docking connection established by the docking facility when the patient table is not arranged exactly in the ideal docking position. The result is then a jerky, lateral movement of the patient couch, which can be felt to be negative by a patient supported on it. The further problem can occur here that, with non-central arrangement of the patient table in relation to the docking facility, damage to the patient table and/or the docking facility occurs. Usually the operator moving the patient table on its opposite side cannot see the docking facility or cannot see it sufficiently well. In order to avoid such problems, it has been proposed for example that two operators be provided on site, of which one for example in front of the patient table can observe the relative arrangement in relation to the docking facility. Even here however deviations from the ideal docking position can still occur.

The quality and the efficiency of the current docking process thus depend on the number and the training of the operators. Even with trained personnel however, time pressures can lead to failed attempts. It is further inconvenient that the operator is focused on the patient table and the medical engineering facility during the docking process, but not on the patient.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 10:
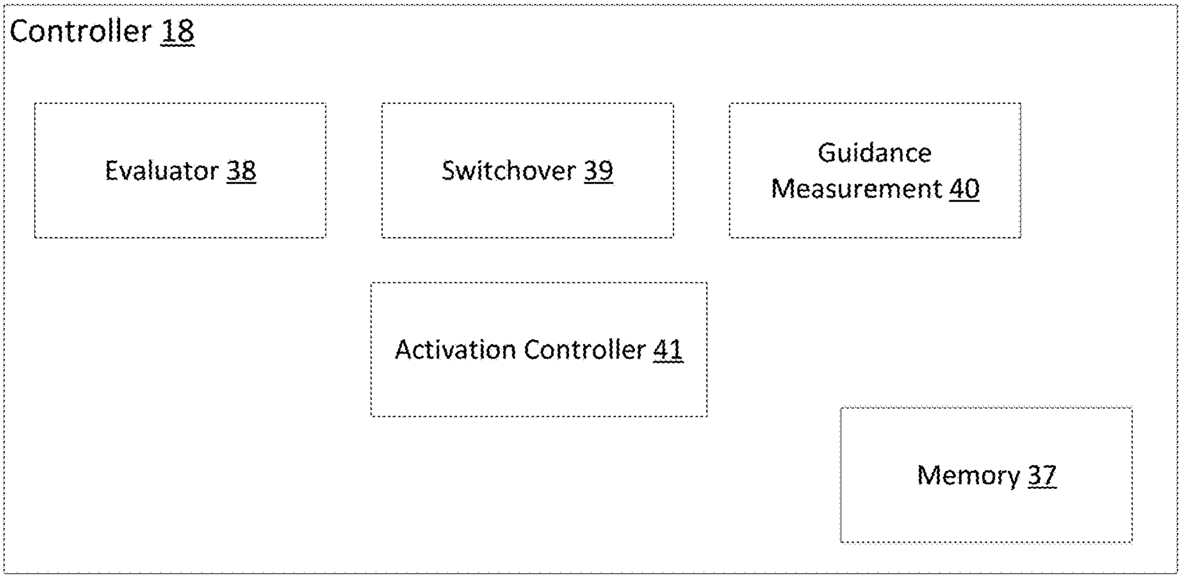

FIG. 10 controller of the docking arrangement according to one or more exemplary embodiments of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is therefore to specify a possibility for improved docking of a patient table onto a medical engineering facility, in particular a magnetic resonance facility, in particular in respect of patient comfort, and for avoidance of damage.

To achieve the objects of the disclosure, provision is made in accordance with the disclosure for a method of the type stated at the outset to, in particular at least partly autonomously, establish a docking position of the patient table necessary for docking by sensor data describing at least the position of the patient table relative to the docking arrangement and/or relative to an environment feature describing a movement trajectory for the docking arrangement being recorded by means of a sensor arrangement of the docking arrangement and evaluated by means of the controller, in order to determine position information describing the position of the patient table, on fulfillment of a switchover condition, which shows the presence of a handover situation and a pure manual operation of the patient table by an operator, a switch being made by the controller into an assistance operating mode of the docking arrangement, wherein, in the assistance operating mode, at least one guidance measure for the patient table for establishing the docking position is determined by the controller by evaluation of the sensor data and is implemented by activation of a functional component of the patient table for assisting the operator.

Here in particular the patient table can have a patient couch that, with a docked patient table, is able to be handed over at least partly to the medical engineering facility.

The docking position is to be understood such that it comprises both a positioning at an optimum docking location and also an optimum docking alignment, which means that the term position is also intended to comprise the orientation (alignment). The purely manual operation of the patient table is to be understood as a normal operating mode of the patient table (and of the docking arrangement), so that it is thus proposed only to offer an, in particular at least partly autonomous, assistance for a short time during the docking process, i.e. the positioning of the patient table relative to the docking facility.

To this end it is proposed that a defined handover situation be provided that, when present (for a short time, i.e. up to the most precise possible establishment of the docking position of the patient table relative to the docking facility), is switched over automatically from the manual mode, i.e. the normal operating mode, to the assistance operating mode, to make it easier for the operator to establish the docking position of the patient table as precisely as possible.

Expediently there can thus be provision for the assistance operating mode to be ended with the docking of the patient table at the docking facility, i.e. in particular the reaching of the docking position or, if provided, the establishment of a docking connection or the acceptance of the patient couch by the medical engineering facility. In an exemplary embodiment, on reaching the docking position, a signal can be sent to the docking facility, which starts the docking automatically.

In this case, for the docking facility, in particular in respect of the establishment of the docking connection and/or also for acceptance of the patient couch from the patient table into the medical engineering facility, and/or for means for the handover of the patient couch back on to the patient table, ultimately any given embodiments, as are basically known in the prior art, can be provided for the docking facility. The medical engineering facility may involve a magnetic resonance facility with a cylindrical patient tunnel, into which the handed-over patient couch is moved.

The patient table, as basically known, can have a carrier facility, in particular a pedestal, for the patient couch, wherein the patient couch can be supported movably on the carrier facility, for example by means of a guidance facility, in at least one direction of movement, in order for example to make possible the handover of the patient couch to the medical engineering facility. Usually the direction of movement involves the longitudinal direction of the patient couch. Also, with regard to the general realization of the patient table, embodiments basically known in the prior art can be used, wherein however the patient table should be designed to be able to be moved manually and should have the at least one functional component, which is activated by the controller for implementing the guidance measure. Expediently the patient table can also comprise at least one part of the controller, which may be realized entirely or at least for the most part in the patient table. The mobility of the patient table can be established by, in particular at least three, wheels of the patient table.

The basis of the assistance can be provided by determination of a position relative to the docking facility and/or a position relative to an environment feature describing a suitable movement trajectory. In respect of the docking facility the relative position can also be determined indirectly via an additional feature, of which the position relative to the docking facility is known. Such an additional feature can for example be provided on the medical engineering facility and/or define an orientation point. In respect of the at least one environment feature there can be provision for the environment feature to comprise a trajectory line on a floor and/or on a ceiling of the room in which the medical engineering facility is arranged.

Exemplary embodiments of the disclosure make provision for a suitable movement trajectory to be shown by a trajectory line as a help line on the floor or on the ceiling of the room in which the medical engineering facility is arranged. In this context the sensor arrangement can comprise a camera on the patient table, which is directed towards the area in front of said table, which can detect this trajectory line.

The trajectory line can be provided permanently on the floor or on the celling, for example by color or the like, but also temporarily, for example can be projected. A visible trajectory line or generally a visible environment feature has the advantage of also serving as an orientation aid for the operator, and can in particular also serve to mark a spatial portion of the handover situation. Also possible, however, is the provision of the trajectory line or generally of the environment feature (and/or also of the additional feature) at least partly in a non-visible way, but in a way that can be perceived by the at least one sensor of the sensor arrangement. In this way a visual load on the operator, in particular in overloaded environments, is reduced. For example, infrared markings, radio markings and the like can be used.

The embodiment with an environment feature, in particular a trajectory line, can be expedient in a large number of respects. In this way there can be provision for the detection of the environment feature, in particular of the trajectory line, by the camera of the sensor arrangement arranged on the patient table, directed to the area in front of it, and/or the undershooting of a distance from said camera, to be used as at least one handover situation.

Generally, the handover situation can be defined in terms of time and/or space. In this way a time-based handover situation can for example comprise at least a specific period of time since entering a room in which the medical engineering apparatus is arranged, and/or at least one attempt at docking having passed without success. The position information can also be evaluated here for temporal handover situations. Generally, it can also be said that the switchover condition may evaluate the position information in order to check for the presence of the handover situation. Especially expediently however there can be a temporal definition of the handover situation with regard to a workflow, in particular monitored and where necessary assisted in its execution by a monitoring system. In this way there can be provision for the handover situation to comprise the conclusion of a preceding workflow step. A preceding workflow step can for example be entering the room with the medical engineering facility, a sign-on by the operator in the room, a positioning of a patient for the medical engineering facility and the like. The conclusion can be determined automatically, for example by the aforementioned monitoring system and/or once again by evaluation of position information and/or of the sensor data.

In an expedient development there can be provision for the switchover condition additionally to check the fulfillment of at least one boundary condition, in particular a current speed of the patient table falling below a speed threshold value. If a speed threshold value is used, this can also be dependent on further operating situations of the patient table, in particular its orientation to the docking facility and/or to the environment feature, since different speeds can be suitable for different approach angles in order still to find the docking position with assistance. However, it is also conceivable for the boundary condition to relate just to this approach orientation. Boundary conditions in respect of other aspects can also be defined, for example in respect of a free path to the docking position able to be checked by the sensor arrangement or in respect of a free docking position, with the adjustability of components of the patient table, their suitable adjustment and the like.

It is especially advantageous in this context for at least the current non-fulfillment of the boundary condition, at least for a time, in particular within the room in which the medical engineering facility is arranged, to be indicated to the operator optically and/or acoustically.

Dedicated optical and/or acoustic output means of the patient table, of the medical engineering facility and/or the room, or those that can be used in other ways, can be employed for this purpose.

For example, there can be provision in the case of a speed threshold value, at least when the current speed is too high, for there to be an indication of this situation, for example by a red light or an acoustic warning. It is also generally expedient however to indicate the fulfillment of boundary conditions, for example by green light or the like. Further graduations are possible. In respect of the speed there can be provision for example for an indication to be given on a scale with at least one red and/or one green area. For example, colored LEDs or backlit surfaces can be used. An output as a number, for example in an appropriate color and/or flashing if the value is exceeded, can also take place.

In order, with a spatially defined handover situation, where possible to avoid an inadvertent activation of the assistance operating mode when the patient table is moving away from the docking facility, an advantageous development can make provision for the switchover condition additionally to demand a direction of movement of the patient table towards the docking facility. In this way the comfort and the assistance are further improved.

In an exemplary embodiment of the present disclosure, there can be provision for the handover situation (then defined spatially) to comprise position information, which indicates a position of the patient table in a handover area defined relative to the docking position. The handover area can also be defined relative to the environment feature or the described movement trajectory, in particular to the trajectory line.

Defined handover positions for assistance mode are provided by the handover area. To be more easily recognized by the operator the handover area can for example be marked on a floor on which the patient table is moved and/or the medical engineering facility stands, in particular in addition to the trajectory line. The handover area is expediently chosen so that a movement trajectory to the docking position that is as comfortable as possible can be realized for a patient supported on the patient couch, in particular the movement trajectory of the environment feature. To this end the handover area can be defined for example as a function of a most unfavorable possible orientation of the patient table in different directions originating from the docking position or the trajectory line, in that then the distances from the docking position or the trajectory line in the corresponding direction that allow a movement trajectory to the docking position that fulfills comfort conditions for the movement trajectory are chosen. In the case of environment features, the movement trajectory described by these can also fulfill the comfort conditions. In this context, but also in general, the assistance method described can also be referred to as smooth docking.

In forms of embodiment with an environment feature, in particular a trajectory line, which describes a suitable movement trajectory, there can be provision for the guidance measures to be determined with regard to the movement trajectory described, in particular for realization of the described movement trajectory that is as comprehensive as possible. If the sensor arrangement has a camera of the patient table, which is directed to the area in front of it, at least one guidance measure for guidance of the patient table along the movement trajectory described by the environment feature can be determined for example using its image data, as sensor data on detection of the environment feature.

For other cases, or when the environment feature, in particular the trajectory line, is only to be interpreted as a suggestion or orientation, there can be provision, initially by the controller, starting from the current relative position and orientation to the docking position and which may consider further objects detected by the sensor arrangement, in particular collision-relevant objects, for a movement trajectory of the patient table to the docking position to be determined and for the guidance measures for realization of this movement trajectory to be specified. The movement trajectory can also be defined in broad terms, for example as an allowed movement corridor in which the patient table is to move in order to reach the docking position. Based on current position information there can be a respective updating of the movement trajectory. The movement trajectory can, as already mentioned, be specified so that it fulfills at least one comfort condition for the patient. The at least one comfort condition can be implemented as a comfort boundary condition, which will be discussed in greater detail below. Basic procedures for determining such movement trajectories and assigned guidance measures, in particular taking into consideration further dynamic and/or static objects, are basically known from similar or other areas of application, for example in motor vehicles, and can, where necessary in appropriately adapted form, also be employed within the framework of the present disclosure. In particular, in addition to taking into consideration static and/or dynamic objects in the determination of the at least one guidance measure, the docking arrangement can also comprise a collision protection system.

The environment detection given by the sensor arrangement can also be referred to as monitoring. Ultimately options are generated by the controller, based on the position and environment detection, that serve to assist the user. The assistance enables the patient table to be positioned at an optimal angle and optimal distance in relation to the docking facility and the docking can in particular take place without lateral jerking and without causing damage.

To summarize, a smooth docking process is thus provided by the present disclosure, in which the docking position can be reached precisely in a simple way, thus no or barely any jerky movements occur during docking and the patient is moved in comfort, in particular into or onto the medical engineering facility. Through the clearly defined handover area and the guidance measures the personnel learn optimal docking processes, in particular with less autonomous forms of embodiment.

A high precision and accuracy in respect of positioning and alignment of the patient table can be provided, wherein this precision can be provided inclusive of the ability to be repeated accurately in all situations and regardless of the training of the personnel.

In an especially advantageous development of the present disclosure there can be provision for the switch into or out of the assistance operating mode to be indicated to the operator by an optical and/or acoustic and/or haptic indication output by means of at least one output means. In this way the operator is made aware that the switch in operating mode is taking place. In this way the presence of the handover situation, in particular of the handover location in the handover area, is not only recognized by the controller but also by the operator. The latter can adapt the way in which they act according to the assistance operating mode. Such an activation notification is in particular expedient when a guidance measure comprises a longitudinal and/or transverse guidance intervention. With a pure output of guidance notifications, as will be discussed in more detail below, their beginning can already serve as an activation notification.

In this case there can be an acoustic output, however an optical and/or a haptic output means may be used, wherein the output means may be also provided on the patient table and/or on the medical engineering facility. For example, on activation of the assistance operating mode a means of handling, for example a handle, can vibrate in order to output a haptic activation notification. This can in particular be combined with an optical activation notification, wherein an optical activation notification on its own is naturally also conceivable. For example, a light source can light up. In an advantageous embodiment there can be provision for example for at least one status light source, in particular extending longitudinally along at least one side of the patient table, to be used. The use of an extended optical output means advantageously enhances its ability to be noticed. For example, a circumferential status light source can also be used. This can be switched over for example on activation of the assistance operating mode for example to the color green and switched back again on deactivation. A change of color as an optical activation notification is likewise especially striking and therefore easy to notice. In this way the information to the operator is ensured.

Within the framework of the present disclosure various degrees of assistance, which can also be understood as degrees of autonomy, are conceivable.

In one concrete form of embodiment of the present disclosure there can be provision for at least one of the at least one guidance measures to be the output of a guidance notification to the operator, wherein one or the optical and/or acoustic and/or haptic output means is used as a functional component. Thus at least one of the at least one output means already used for the activation notification can also be used for an output within the framework of a guidance measure, or other output means, provided on the patient table and/or on the medical engineering facility, can be used.

In this concrete form of embodiment at least one part of the guidance measures relate at least in part to the output of guidance notifications to at least one output means provided on the patient table and/or on the medical engineering facility and/or easy to see in the operating position by the operator moving the patient table manually, in response to which the movement trajectory to the docking position is accordingly established at least in part by the operator under their own responsibility. Such an embodiment can also be sensible for an at least partly autonomously moved patient table in assistance operating mode, for example in situations when sensor data is partly not able to be acquired and/or is of lower quality and/or critical maneuvering situations with dynamic objects and/or objects to be protected, so that then, at least temporarily, more responsibility can be handed to the operator.

In this case it should be noted once again at this point that such output means for the activation notification and/or the guidance notification can also be used for the avoidance of collisions. For example, possible collision objects can be highlighted and/or displayed in accordance with a collision protection system and/or by another evaluation of the sensor data by means of the output means. The operator can then move them out of the way. This is in particular expediently possible for image data of a camera detecting an area in front of the patient table. This image data can then be shown with collision objects highlighted.

In concrete terms, with the output of guidance notifications, for example with regard to the steering behavior, i.e. the transverse guidance, provision can be made for the output of arrows, the size of which can depend on the strength of the steering intervention, and/or a haptic output on a side that is to be steered towards, the strength of which can depend on the strength of the steering intervention, and/or an acoustic output as a kind of parking assistance system (intermittent output of tones, the frequency of which reflects a variable, here for example the steering intervention strength or a change that is still needed), wherein right and left can be assigned different pitches. Analog variants can also be provided for longitudinal guidance indicators, wherein in particular an output comparable with a parking assistance system is expedient, in which for example the approach to the docking facility or docking position or also the movement trajectory described by the environment feature can be shown.

In exemplary embodiments there can be provision for a required movement corridor to be output to the operator as a guidance notification on an optical output means.

This is undertaken in particular overlaid with image data of the area in front of the patient table. This can in particular also show the trajectory line. In this case it should be noted that just the output of image data with the trajectory line alone, that is in particular without movement corridor, can act as a guidance notification. The camera can also be active at least from time to time in normal operating mode in order to facilitate the operator with approaching the trajectory line or in general an environment feature provided on the floor that is optically visible. To this end a display can be provided in the area of a handling facility as an optical output means.

In exemplary embodiments there can be provision for the guidance notification to be a transverse guidance notification. For example, an indication can be given by optical and/or haptic output means arranged on the right and left, as to where to steer towards in order to reach the docking position. Here output means can also be arranged on the medical engineering facility or output means provided in any event on the medical engineering facility, for example lights, can be used. Then the operator can keep their eye on the actual destination. The optical output means can generally be in the shape of arrows. Extended optical output means, via which, with the aid of an illuminated position or an illuminated length, a strength of the recommended steering intervention can be shown, are also conceivable. In respect of haptic output means there can be provision for haptic output means to be provided on a handling facility, for example a handrail, on the left and on the right. A vibration can be given as a guidance notification of where to steer. The strength of the recommended steering intervention can be encoded via the vibration. Overall, optical output means arranged on a handling facility or adjacent thereto have the advantage that the visualization is close to the function.

Such an exemplary embodiment, in which the operator receives guidance notifications, but still moves the patient table entirely by themselves, can be referred to as degree of assistance of 1 (or in the extended interpretation of autonomy also as degree of autonomy of 1).

In one or more exemplary embodiments, the docking position may be implemented at least in part autonomously by means of corresponding actuators of the patient table as functional components. In such cases it should already be noted at this point that patient tables with transverse guidance and/or longitudinal guidance actuators have already been proposed in the prior art, wherein then the actuators are able to be activated for the actuation of operating elements. This involves for example a, also just servo-type simplification of the manual movement of the patient table. For example, operating elements have been proposed in which speeding up and/or slowing down is by means of a rotary handle and/or brakes are actuated by a brake lever. For steering, levers or movable rotary handles have been proposed. Thus, if these types of longitudinal guidance and transverse guidance actuators are provided in assistance operating mode for autonomous guidance, these can also be used in manual operation (normal operating mode) via corresponding operating elements.

In an exemplary embodiment of the present disclosure, there is provision that, for a guidance measure describing a steering intervention, at least one steering actuator of the patient table is activated as a functional component for at least part implementation of the steering intervention and/or with a guidance measure describing a longitudinal guidance intervention at least one longitudinal guidance actuator of the patient table is activated as a functional component for at least part implementation of the longitudinal guidance intervention. It is thus conceivable to automate the transverse guidance and/or the longitudinal guidance at least partly, thus to provide a corresponding degree of autonomy. Here, there may be a full implementation of the steering intervention and/or longitudinal guidance intervention, wherein only a part implementation can also be understood as a guidance notification.

Steering actuators in such cases can be usual actuators acting on the alignment of wheels of the patient table, wherein steering actuators acting both on of a part of the wheels and also on all of the wheels are conceivable. For example, the steering actuator can serve for automatic track guidance and/or the steering actuator can provide active steering on the chassis. Longitudinal guidance interventions comprise acceleration interventions and braking interventions. Accordingly, the longitudinal guidance actuator can in particular comprise a drive actuator and/or a brake actuator. Depending on the extent to which an autonomy of the patient table during the assumption of the docking position is desired or, to put it another way, how the responsibility for the movement of the patient table is to be supported, guidance measures in respect of actuator systems that go to different lengths can be allowed. For example, it is conceivable, as will be discussed in greater detail below, to limit the autonomous guidance of the patient table to the transverse guidance and to continue to leave the longitudinal guidance to the operator. This then specifies whether the patient table moves. Regardless of this, exemplary embodiments are also naturally conceivable in which steering interventions and/or longitudinal guidance interventions only up to a particular strength are permitted as guidance measures and, for maneuvers that go beyond this, guidance measures are specified that are left to the operator by guidance notifications.

In particular in cases in which the presence of the operator at the patient table in assistance operating mode is still needed, but also for advanced autonomy, an advantageous embodiment makes provision that, for one of the guidance measures that relates to an action of the operator which opposes a steering intervention and/or a longitudinal guidance intervention, the guidance measure is aborted. In this case a guidance measure, in concrete terms the corresponding steering intervention and/or longitudinal guidance intervention, is able to be manually overridden by the operator in such an embodiment. If the operator is monitoring the at least partly autonomous operation of the patient table and they judge that the guidance measure is rather unsuitable, i.e. the proposed option is rejected, this can be overridden and aborted by a powerful counter steering or generally steering in the other direction. Here a suitable patient table sensor system is used to monitor whether an action opposing the intervention is available to the operator. In this case, a check can be carried out to determine whether the strength of the opposingly directed action exceeds a threshold value. If this is the case, the opposingly directed action is identified as steering in the opposite direction and the guidance measure is aborted.

A degree of assistance of 2 (or degree of autonomy of 2) can be assigned to an exemplary embodiment in which a transverse guidance occurs autonomously through transverse guidance interventions, but the longitudinal guidance is left to the operator however and in which transverse guidance interventions can be overridden.

In the context of an at least partly autonomous movement of the patient table by the controller, in an expedient embodiment of the present disclosure there can be provision, on the patient table, in particular on a handling facility for the operator, or separately from this, for a handling detection means and/or a handling operating element, the handling data of which is evaluated by the controller for determination of handling information showing the monitoring and/or readiness for action by the operator, wherein the activation of the steering actuator and/or of the longitudinal guidance actuator only occurs if monitoring and/or handling readiness is indicated. By means of such a handling detection means and/or handling operating element a check can be carried out to determine whether the operator indicates monitoring and/or the operator is ready to act, i.e. reacting quickly in case of doubt, can take over the guidance of the patient table manually. Expediently this type of handling detection means and/or handling operating elements can be provided on, in particular also adjacent to, handling facilities of the patient table, for example to handles or rails that the operator can grip in order to move the patient table manually. A handling detection means can for example check whether an operator's hand is gripping a handling facility, and thus be designed for example as a capacitive and/or inductive sensor. In an exemplary embodiment, a handling operating element may be used with which the operator must actively show that they are monitoring the movement and/or is at the patient table and are ready for action.

It is particularly expedient in this case for the handling operating element to comprise a dead man's handle to be put actively into an actuation setting against a reset force. For example, the handling operating element can comprise a lever arranged adjacent to a handle and/or a rail as a handling facility, which can be moved against the reset force towards the handle or the rail. Such a dead man's handle can also be referred to as a Dead Man Grip (DMG).

What can generally be said about the handling operating element is that ultimately it can be understood such that, with its actuation, the operator enables the autonomous movement of the patient table or with the ending of the actuation can also stop it. Embodiments are also conceivable in which the handling operating element is not provided on the patient table, but on or as an additional operating device. In this case it merely indicates monitoring where necessary.

A degree of assistance of 3 (or degree of autonomy of 3) can be assigned to an exemplary embodiment in which the longitudinal guidance and the transverse guidance occurs autonomously through guidance interventions and a readiness for action is indicated by a handling operating element, in particular a dead man's handle. Here too an override can still be made possible.

In particular in respect of advanced autonomy, i.e. when in particular monitoring and/or readiness for action by the operator is no longer demanded, but also in other general cases, it can be expedient for the docking arrangement, in particular the patient table, to have an emergency stop switch, wherein the controller ends the assistance operating mode on actuation of the emergency stop switch. Here, in particular, the movement of the patient table is also ended with the ending of the assistance operating mode; in other words, the patient table is stopped. The emergency stop switch is available in cases of emergency for a manual intervention, i.e. an emergency stop.

A degree of assistance of 4 (or degree of autonomy of 4) can be assigned to an exemplary embodiment, in which the longitudinal guidance and the transverse guidance takes place autonomously through guidance interventions and an emergency stop switch is provided.

As already mentioned, various degrees of autonomy of the patient table in the assistance of the operator are conceivable. It has proven to be especially expedient for guidance measures related exclusively to the transverse guidance to be determined and implemented, so that the longitudinal guidance continues to be left completely manually to the operator. In such an embodiment, the operator still has to push the patient table them self. The fact that the operator himself or herself is responsible for the longitudinal guidance means that a greater share of the overall responsibility lies with them. In particular, the speed of the patient table continues to be specified by the operator. Despite this the docking position can be activated precisely by the autonomous steering of the patient table. In this way operation by a single person is in particular possible.

In summary and in an overview various degrees of assistance or degrees of autonomy are possible in the assistance operating mode. In an exemplary embodiment, only an appraisal of the situation is carried out and options are determined and proposed, in particular by the guidance notification. One embodiment goes one step further, in which the transverse guidance by steering actuators is taken over automatically by the controller and corresponding guidance measures, but the longitudinal guidance remains with the operator, wherein the operator can override opposingly directed actions (degree of assistance of 2).

A further autonomy is achieved when both the longitudinal guidance and also the transverse guidance are implemented automatically via guidance measures actuating corresponding actuators of the patient table, but the operator monitors the movement and/or remains ready to act, in particular at the patient table itself and may indicate this by the handling operating element, in particular the dead man's handle, (degree of assistance of 3). The operator thus monitors the movement of the patient table and can, for example by letting go of the handling operating element, stop said table or where necessary in forms of embodiment even take it over them self by opposingly directed actions. In such an embodiment for example, when static and/or dynamic objects do not have to be taken into consideration or only to a restricted extent, and/or no collision protection system is available, the operator can monitor the movement for potential collisions.

Finally, an embodiment is also conceivable in which the operator no longer monitors the movement and must enable it by means of a handling operating element, in particular a dead man's handle. The operator can thus devote him or herself to other tasks. In this regard the sensor arrangement and the actuators, in particular the at least one steering actuator and the at least one longitudinal guidance actuator, are to be designed for safety, in particular to fulfill at least one safety standard, for example by means of redundant embodiment, plausibility checking and the like. Thus, collisions and the like can be avoided. In case of emergencies, the emergency stop switch on the patient table is then expediently available for a manual emergency stop (degree of assistance of 4).

In an exemplary embodiment, there can be provision for the controller, during the determination of a steering intervention and/or of a longitudinal guidance intervention, to be embodied to take into consideration at least one comfort boundary condition related to the comfort of a patient supported on the patient couch. For example, the strength of interventions that are carried out automatically can thus be restricted in order to ensure a movement of the patient table for the patient that is as comfortable as possible. While in respect of the longitudinal guidance the acceleration values and/or speed values of the longitudinal guidance intervention can especially expediently be restricted by comfort boundary conditions, an exemplary embodiment in respect of steering interventions makes provision for the comfort boundary condition to comprise a maximum permissible curve radius. Also, in particular with speed controlled by the controller, the comfort boundary condition can comprise a maximum permissible angular acceleration. In this way in particular jerky movements during the docking process to prepare for docking can be avoided, so that the patient can be moved to the medical engineering facility in comfort. It is therefore possible to realize a pleasant travel speed and a pleasant negotiation of curves for the patient.

In respect of the sensor arrangement there can be provision for at least one part of the sensors of the sensor arrangement to be arranged on the patient table. For example, the proximity sensors of the sensor arrangement detecting the surroundings of the patient table directed to the surroundings can be provided on or behind an outer cladding of the patient table. The position sensors of the patient tables for determining the position, for example a position determination system, can also be provided inside the patient table. In an exemplary embodiment, all sensors of the sensor arrangement can be arranged on the patient table. If the controller is also located completely in the patient table, all components necessary for implementation of the inventive method can be arranged in the patient table. It can also be expedient to use external sensor systems, in particular for environment detection, since for example proximity sensors of the sensor arrangement arranged on a ceiling of a room in which the medical engineering facility, and/or proximity sensors of the sensor arrangement arranged on the medical engineering facility can have a better overview or a more suitable detection area.

A sensor arrangement can be used which has:

at least one optical sensor, in particular a camera, such as a three-dimensional (3D) camera, and/or at least one distance sensor, in particular a radar sensor and/or an ultrasound sensor.

These types of sensors are frequently used in applications in which objects, such as the patient table here, are moved automatically. Thus, for example there can be provision for a camera-based localization and/or environment monitoring to be used, wherein in addition or as an alternative, in particular also in a context in which static and/or dynamic objects are taken into consideration and/or in a context of avoiding collisions, distance sensors, for example radar sensors and/or ultrasound sensors, are useful.

As already mentioned, the present disclosure can be applied especially expediently when the medical engineering facility is a magnetic resonance facility. In this context an especially expedient embodiment in respect of the determination of the position information of the patient table is conceivable, which makes use of the magnetic field present outside the patient tunnel of the magnetic resonance facility, which can be expressed as the stray field of the magnetic resonance facility. In concrete terms there can then be provision for the sensor arrangement to comprise at least one magnetic field sensor, in particular a Hall sensor, of the patient tablet, wherein for determination of the position information the sensor data of the magnetic field sensor is reconciled with a magnetic field map of the stray field of the magnetic resonance facility in its environment. Expediently in this case a number of magnetic field sensors can be employed in order to enhance the accuracy of the localization of the patient table and remove any ambiguities.

In summary and in general terms, within the framework of the present disclosure at least one transverse guidance actuator, in particular a steering actuator, and/or at least one longitudinal guidance actuator, in particular a drive actuator and/or a braking actuator, and/or at least one output means of the patient table can be used as functional components of the patient table.

In addition to the method, the present disclosure also relates to a docking arrangement that may include a docking facility for a patient table, a controller, a sensor arrangement and the patient table, which has at least one functional component and which, during docking of the patient table at the docking facility with a medical engineering facility to which the docking facility belongs, is able to be connected, wherein the controller is embodied to carry out the inventive method. All embodiments regarding the inventive method can be transferred by analogy to the inventive docking arrangement, with which the advantages already mentioned can thus likewise be obtained.

In this case, it should be noted once again at this point that, as mentioned, it is conceivable for the controller and the sensor arrangement to be integrated completely into the patient table, so that the inventive method can also be carried out by means of the patient table on its own. In this case a conceivable patient table thus has a controller, a sensor arrangement and at least one functional component, wherein, during docking of the patient table at a docking facility of a medical engineering facility, the patient table is able to be connected to the medical engineering facility, wherein the controller is embodied for carrying out the inventive method. Here too, the embodiments regarding the inventive method continue to apply accordingly.

In particular the controller has the following, both for the inventive docking arrangement and also for the conceivable patient table:

an evaluation unit for evaluation of sensor data recorded by means of the sensor arrangement, describing at least the position of the patient table relative to the docking arrangement and/or relative to an environment feature describing a movement trajectory to the docking arrangement, in order to determine position information describing the position of the patient table, a switchover unit for monitoring the fulfillment of a switchover condition, which indicates the presence of a handover situation and a purely manual operation of the patient table by an operator, and, on fulfillment of the switchover condition, for switching into an assistance operating mode, a measure determination unit for determination of at least one guidance measure for the patient table for establishing the docking position by evaluation of the sensor data in the assistance operating mode, and an activation unit for implementation of the guidance measure by activation of a functional component of the patient table for assisting the operator.

It can generally be said that the controller can comprise at least one processor and at least one memory means. The functional units mentioned above, and further units can be realized by hardware and/or software.

The inventive method can be realized as entirely computer-implemented. Therefore, a computer program can also be provided. The computer program has program means that, when the computer program is executed on a controller of an inventive docking arrangement, cause said facility to carry out the steps of an inventive method. The computer program can be stored on an electronically readable data medium.

Controller

Figure 1:
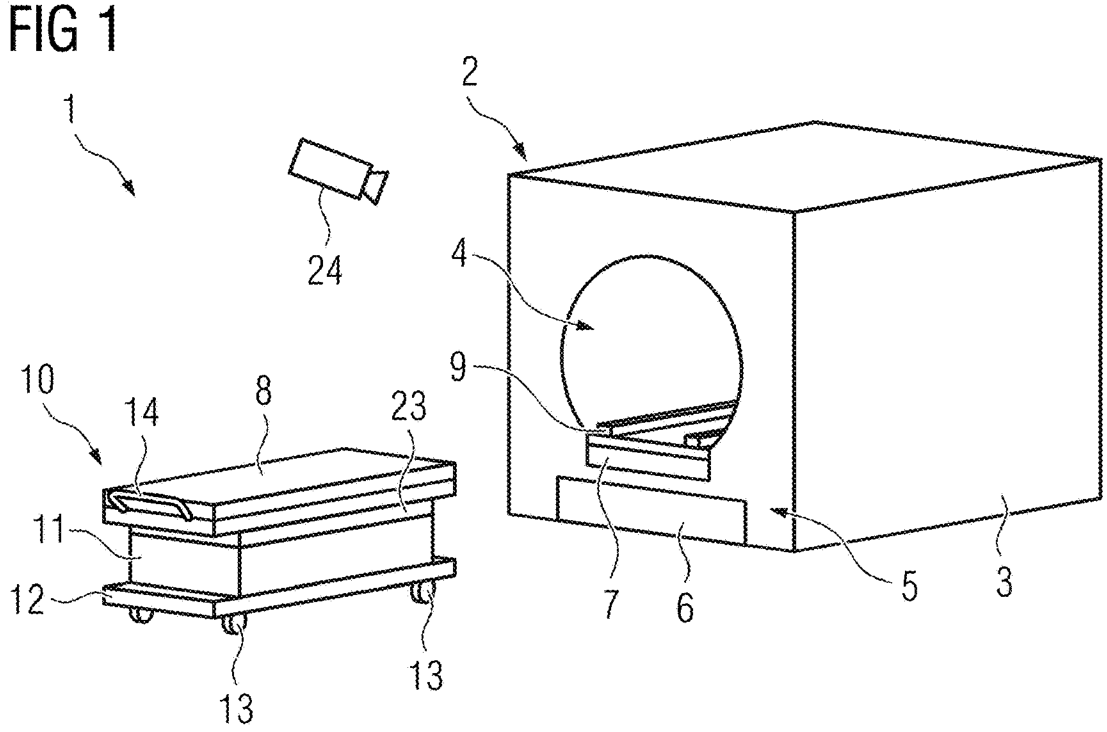
FIG. 1 shows a view of a docking arrangement according to one or more exemplary embodiments of the disclosure.

FIG. 1 shows a schematic, perspective view of components of an inventive docking arrangement 1 according to the disclosure. A medical engineering facility 2 in this figure is embodied as a magnetic resonance facility 3, which has a cylindrical patient tunnel 4. A docking facility 5 is further provided, which in this figure has a lower docking means 6 and an upper drawing-in apparatus 7 for drawing a patient couch 8 into a guidance facility 9 inside the patient tunnel 4, so that a patient supported on the patient couch 8 can be positioned inside the patient tunnel 4 for imaging purposes.

Figure 2:
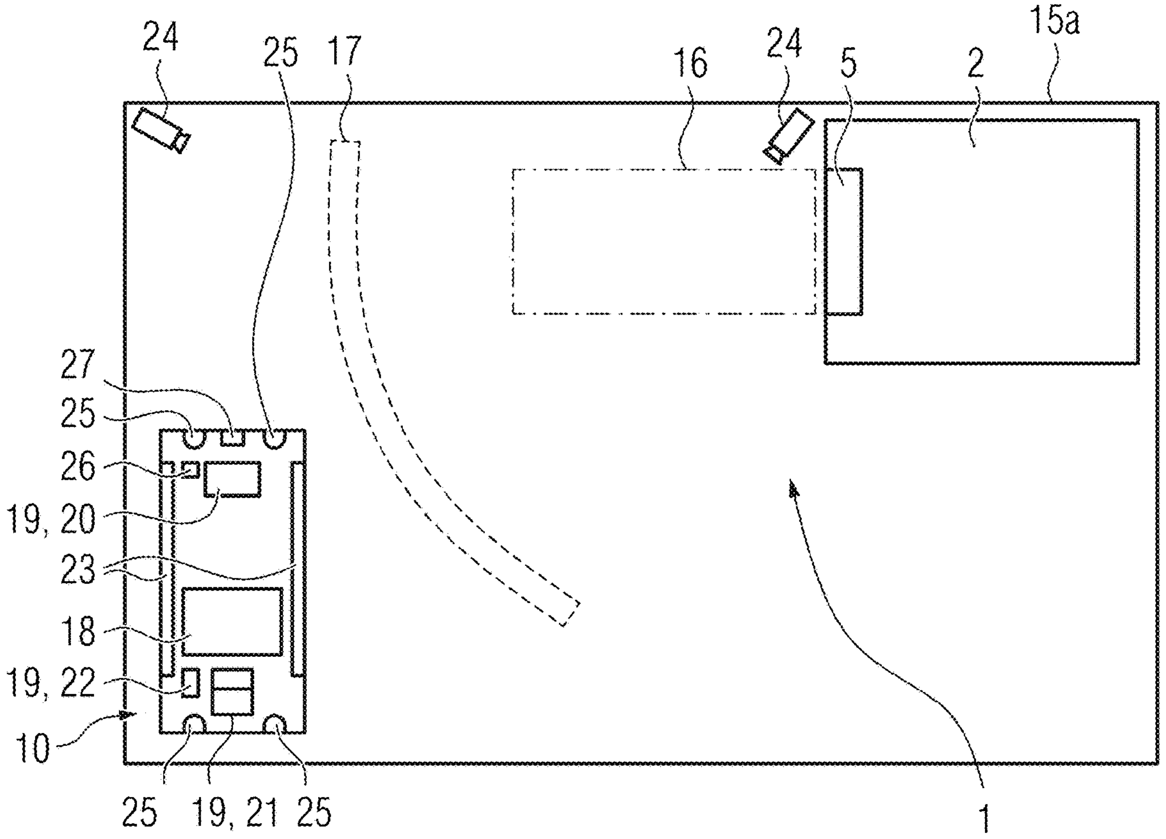
FIG. 2 shows a schematic, plan view of a room in which the docking arrangement is arranged, according to one or more exemplary embodiments of the disclosure.

In the present example, the patient table 10 of the docking arrangement 1 may have a carrier facility 11, on which the patient couch 8 is supported movably in the longitudinal direction of the patient couch 8 by means of a patient table-side guidance facility (not shown in more detail). The carrier facility 11 has a drive mechanism 12 with wheels 13 as well as a handling facility 14, for example a handle and/or and handrail, so that the patient table 10 can be moved manually by an operator. This ability to be moved manually in normal operating mode can be assisted by means of actuation systems able to be activated by operating elements on the handling facility 14. The patient table 10 can further, on reaching a handover area on the way to the docking facility 5, assist the operator in a temporary assistance operating mode with various degrees of assistance during positioning, in particular for an optimal docking position. In order to explain this more precisely, FIG. 2 shows a purely schematic overhead view of a first variant of a room 15*a*, in which the medical engineering facility 2 is arranged. The patient table 10 has already been brought into this room 15*a*. The docking position 16 which is ideal for docking, comprising a docking location and a docking orientation in front of the docking facility 5 is indicated schematically. Here the docking means 6 has a receptacle for the forward area of the drive mechanism 12 as well, and during docking establishes a docking connection between the patient table 10 and the docking facility 5. In this way for example the patient table 10 can be locked in its docked position.

In order to assist the operator in this case to establish the docking position 16 as accurately as possible, a handover area 17 is defined and is also marked on the floor of the room 15*a*. The location of the handover area 17 has been specified so that, independently of the orientation of the patient table 10 on entering said area, movement into the docking position 16 fulfilling a comfort boundary condition is possible.

In order to provide the assistance, the patient table 10 may include a controller (control facility) 18 may be adapted to, in assistance operating mode, determine guidance measures in order to move the patient table 10 at least partly autonomously into the docking position 16 or to provide the operator with assistance here. The controller 18 may be adapted to generate one or more control signals configured to control movement of the patient table 10. In accordance with the guidance measures various functional components 19 of the patient table 10 are activated, which in the present example, comprise a steering actuator 20, longitudinal guidance actuators 21 (in the present example a drive actuator and a brake actuator) as well as in part output means 22 of the patient table 10. In the present example the patient table 10 also comprises as further output means 23 status light source extending on the sides of the patient table 10, which are activated by the controller 18 when the switch is made into assistance operating mode for output of an activation notification, in order for example to show a green light for the duration of the assistance operating mode. The steering actuator 20 and the longitudinal guidance actuators 21 are optional in this case and, as will be discussed in greater detail below, are not needed or not needed fully for lower degrees of assistance, in particular degrees of assistance of 1 and 2. The controller 18 may include processing circuitry that is adapted to perform one or more functions and/or operations of the controller 18. Additionally, or alternatively, one or more components of the controller 18 may include processing circuitry that is adapted to perform one or more respective functions and/or operations of the component(s).

In order to be able to establish when the switch is to be made from the normal operating mode into the assistance operating mode, thus when a switchover condition is fulfilled, in the present example a sensor arrangement is also provided as part of the docking arrangement 1, which in the present exemplary embodiment has sensors, in the present example cameras 24, actually 3D cameras, outside of the patient table 10 and also sensors, in the present example distance sensors 25, actually ultrasound sensors and/or radar sensors, and magnetic field sensors 26, in the present example Hall sensors, as part of the patient table 10. Moreover, the patient table 10, as part of the sensor arrangement in the present example, itself has cameras 27 directed to the area in front of it. Exemplary embodiments are also conceivable in which only sensors of the patient table 10 are used as part of the sensor arrangement.

The magnetic field sensors 26 ultimately measure the stray field of magnetic resonance facility 3 present at their location in the present example. With the aid of a magnetic field map of the stray field, position information for the position of the patient table 10 relative to the docking facility 5 is able to be determined reliably from this, in particular when a number of magnetic field sensors 26 are used and/or also for determination of the direction of the local stray field. This can be plausibility checked with the sensor data of other sensors of the sensor arrangement describing the relative position.

From the sensors of the sensor arrangement the controller 18 derives position information, with the aid of which it can be determined whether, as part of the switchover condition, the patient table 10 is located in the handover area 17 and is moving towards the docking facility 5. This thus involves a spatially defined handover situation. As part of the switchover condition it is further checked whether purely manual operation, i.e. the normal operating mode, still obtains at this time. If the switchover condition is fulfilled, a switch is made into the assistance operating mode and this is indicated, as described, by means of the output means 23 (status light sources). In this way the operator is notified that the assistance operating mode is now active.

In one or more exemplary embodiments, the switchover condition can check for the presence of a temporally defined handover situation, for example the conclusion of a preceding workflow step.

Figure 3:
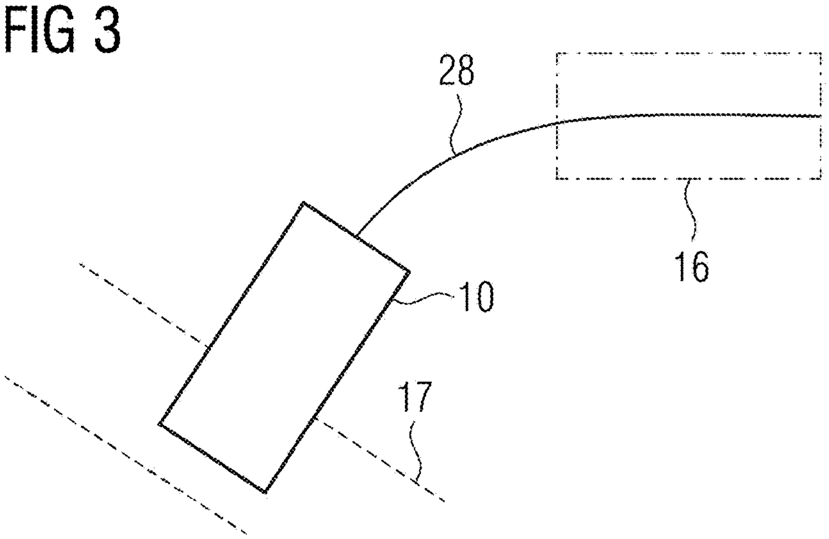
FIG. 3 shows a diagram illustrating the planning of a movement according to one or more exemplary embodiments of the disclosure.

In assistance operating mode the controller 18, in a first group of concrete exemplary embodiments, determines as a basis for determination of the guidance measures, as is shown in FIG. 3, a movement trajectory 28 to the docking position 16. This movement trajectory 28 (and thus also the guidance measures resulting therefrom) is defined so that the comfort boundary conditions for the patient already mentioned, in particular with regard to the behavior when negotiating curves, are fulfilled. For example, a maximum permitted curve radius and/or a maximum permitted angular speed can be defined; moreover, a restriction of the acceleration and/or of the speed during the longitudinal guidance can also be defined.

In the determination of the movement trajectory 28 the controller 18 expediently also takes into consideration static and/or dynamic objects in the area of movement, which are detected by the sensors of the sensor arrangement. As an alternative or in addition, the docking arrangement 1 can also comprise a collision protection system. Objects also shown as objects for which a potential collision has been established are highlighted on an image of one of the cameras 24, 27 using one of the output means for the operator for example, so he or she can remove them.

Figure 4:
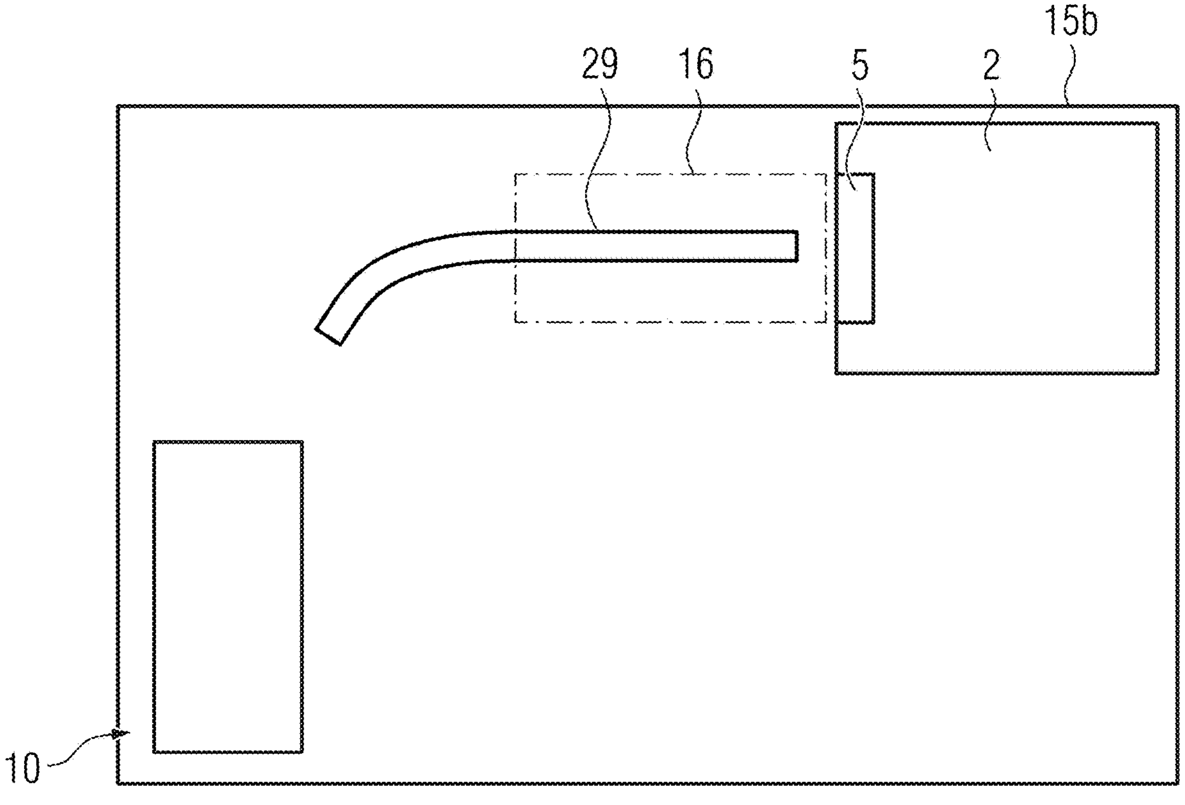
FIG. 4 shows a schematic, plan view of a room in which the docking arrangement is arranged according to one or more exemplary embodiments of the disclosure.

FIG. 4 shows a purely schematic overhead view of a second variant of a room 15*b*. For the sake of clarity and brevity, the components of the patient table 10 and also the cameras 24 are no longer shown here, since there is no change in this regard.

Unlike in FIG. 2, the handover area is not marked on the floor in room 15*b*, but this can still be done as an option when a corresponding spatial handover situation is used. Instead, in the present example, a trajectory line 29, which is applied to the floor as a kind of assistance line, is used as an environment feature describing a suitable movement trajectory to the docking position 16. This trajectory line 29 can in particular also be detected with the camera 27 of the patient table 10 directed to the area in front of it.

In the embodiment of the room 15*b*, the trajectory line 29 may be used in respect of the switchover condition and/or as a basis for the assistance. In respect of the switchover condition the detectability of the trajectory line 29 and/or a distance below a maximum distance to this is checked as the present handover situation by the controller 18. The controller 18 can further evaluate the sensor data of the sensor arrangement with regard to the relative position of the patient table 10 in relation to the movement trajectory described, in particular as an alternative or in addition to the relative position in relation to the docking facility 5.

Based on this, the assistance and thus the determination of the guidance measures for room 15*b* or other embodiments using environment features describing suitable movement trajectories can relate to the use of the movement trajectory described, i.e. here a travel along the trajectory line 29.

The controller 18 can also be embodied, within the framework of the switchover condition, to check the fulfillment of at least one boundary condition for the switchover to the assistance operating mode. If this is not fulfilled, this can be indicated to the operator—also already beforehand—by means of the output means 22 of the patient table 10, in particular of a dedicated output means 22. In concrete terms for example a boundary condition can check whether the speed of the patient table 10 lies below a threshold value. If the speed is too high meaningful assistance can namely not be possible.

Figure 5:
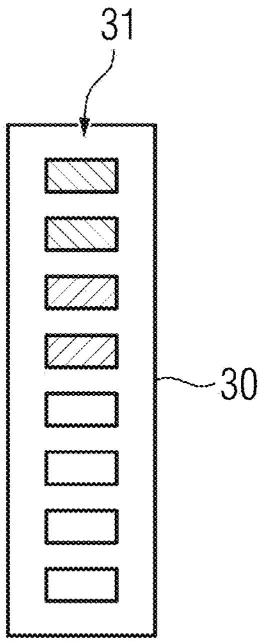
FIG. 5 shows a dedicated output interface adapted to fulfill a boundary condition according to one or more exemplary embodiments of the disclosure.

A dedicated output means 22 provided in this regard, for example in the area of the handling facility 14, in the form of a scale 30 consisting of colored light sources able to be backlit, in particular LEDs, is shown in FIG. 5. The two topmost light sources 31, shown cross-hatched, are red and show if the speed is too high. These are followed by yellow and green light sources 31 for lower speeds. Other embodiments are naturally also conceivable, for example text outputs, a single light source, which can show a green, yellow or red light, and even acoustic output means 22.

The degree to which the assistance and also automation by the controller 18 occurs in the assistance operating mode differs depending on the actual exemplary embodiment, so that differences can also be produced in respect of the concrete embodiment of the patient table 10. The concrete exemplary embodiments explained below for various degrees of assistance are independent of how precisely the switchover condition is designed and whether the guidance measures relate to the docking position 16 or to the movement along the movement trajectory described by the trajectory line 29.

In a first, concrete exemplary embodiment to which a degree of assistance of 1 can be assigned, the guidance measures involve the activation of output means 22 for output of a guidance notification to the operator, without there being any steering interventions and/or longitudinal guidance interventions. The operator is solely responsible for the movement of the patient table and merely receives the guidance notifications, which can be related to the transverse guidance for example (for example whether and how strongly the table should be steered manually to the left and/or to the right).

Figure 6:
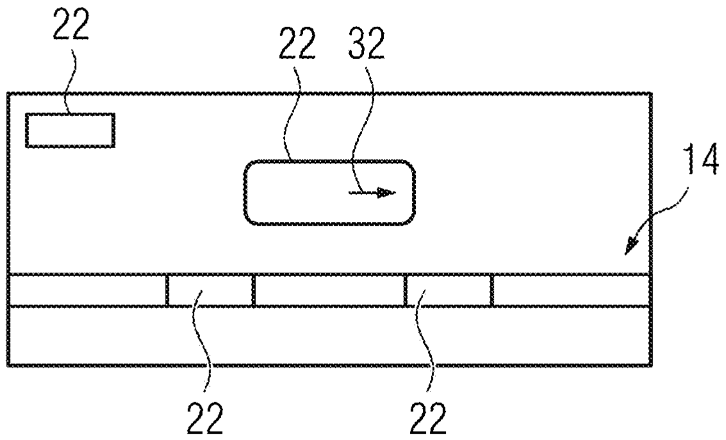
FIG. 6 shows a handling area of a patient table according to one or more exemplary embodiments of the disclosure.

To this end, FIG. 6 shows a possible embodiment of the handling area of the patient table 10 with the handling facility 14, here a handrail. It can be seen that a guidance notification related to the transverse guidance can be output on the optical output means 22 in the form of an arrow 32. A guidance notification in respect of a direction to steer can likewise be given by means of haptic output means 22 in the handling facility 14, wherein in the present example the right-hand haptic output means 22 can vibrate. An acoustic output means 22 is also conceivable, indicated at the top left in FIG. 6. The guidance notifications in this case can merely relate to the transverse guidance, so that the longitudinal guidance, thus in particular the speed of the patient table 10, can be left entirely to the operator. In exemplary embodiments it is however also conceivable to output guidance notifications also related to the longitudinal guidance, for example acoustically as a kind of parking assistance system.

It is also conceivable, as an alternative or in addition, to use output means (not shown) on the medical engineering facility 2, for example with the magnetic resonance facility 3, above or next to the patient tunnel 4. In particular, an optical output means can be assigned to the left, one to the right, in order to indicate in which direction the table is to be steered. In this case output means provided in any event can be used.

Finally, a display in the handling area can also be employed as the optical output means 22, which can show a movement corridor to be used, in particular overlaid in relation to the image data of the camera 27.

It should be noted that even with at least partly autonomous guidance in the assistance operating mode there can be recourse to an embodiment in which guidance notifications can be output in this way as guidance measures, for example when critical situations and/or low-value/no sensor data is available.

In a second concrete exemplary embodiment (degree of assistance of 2) in the present example the transverse guidance is automated, meaning that the patient table 10 moves, at least as regards the transverse guidance, automatically. This is achieved by activation of the steering actuator 20. In this case however the automatic movement is constantly monitored by the operator. By merely the transverse guidance being taken over the operator must necessarily still push the patient table 10 manually, so that this monitoring activity is required in order to bring about any effective movement. The possibility exists here for the operator of overriding, i.e. steering in the opposite direction, in order to abort a guidance intervention.

Figure 7:
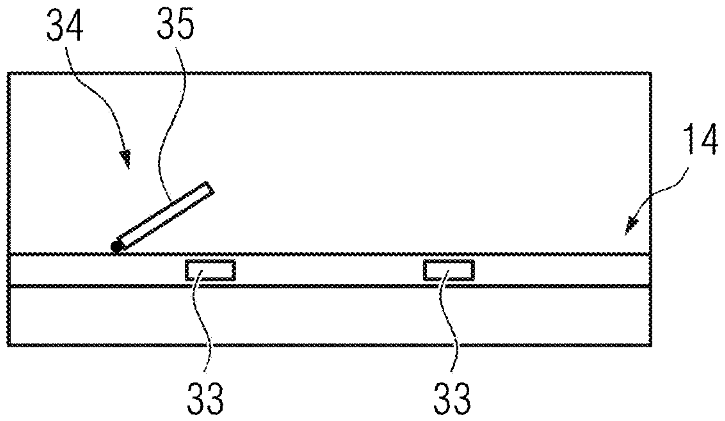
FIG. 7 shows a handling area of a patient table according to one or more exemplary embodiments of the disclosure.

In a third concrete embodiment (degree of assistance of 3) not only the transverse guidance but also the longitudinal guidance is implemented by guidance interventions. To this end the controller 18 determines longitudinal guidance interventions and activates the longitudinal guidance actuators 21 accordingly. In order, with this third concrete embodiment, in which the longitudinal guidance is also taken over automatically by the controller 18 and corresponding guidance measures are taken over, to ensure that the operator is ready to act, two options are shown schematically in FIG. 7, which once again show the handling area. In this way there can be provision on the one hand, within the handling facility 14, for providing handling detection means 33, for example capacitive and/or inductive sensors detecting the hand of the operator, which thus deliver handling data which shows the presence of the hand.

However, a handling operating element 34, in the present example a dead man's handle 35 which can be moved into an actuation setting against the resetting force, may be provided on the handling facility 14. In the example shown, when the handling facility 14 embodied as a handrail is gripped by the operator the dead man's handle 35 can also be easily operated in order to indicate the monitoring and the readiness for action and to enable the autonomous movement. If the actuation of the dead man's handle 35 is ended, any movement is also stopped. Therefore, the dead man's handle 35, or generally the handling operating element 34, can also be provided externally to the patient table 10, for example as an additional operating device or in an additional operating device when the readiness for action is less relevant.

The advantage of an arrangement on the patient table 10 and thereby of directly establishing a readiness for action is however that here too the possibility exists of individual guidance measures or groups of guidance measures being able to be overridden by the operator. If an operator action directly opposing the intervention of the guidance measure is established by the controller 18, the strength of which exceeds a threshold value, here too the guidance measure is aborted, as it is in the second concrete exemplary embodiment. In this way the operator can actively intervene.

Figure 8:
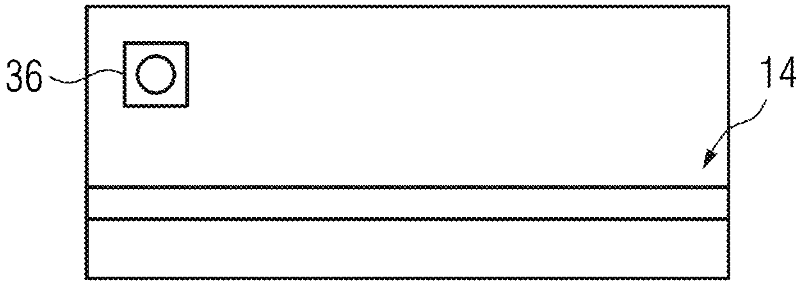
FIG. 8 shows a handling area of a patient table according to one or more exemplary embodiments of the disclosure.

In a fourth exemplary embodiment (degree of assistance of 4) once again the longitudinal and the transverse guidance is completely automated. However, monitoring or readiness for action by the operator is not absolutely necessary since the sensor arrangement, the controller 18 and the actuator system are designed safely enough, in particular fulfill at least one safety standard. In this case the patient table 10 travels, in particular on the movement trajectory 27 or the trajectory line 29, explicitly and smoothly into the docking position 16, while the operator can devote him/herself to other tasks. Despite this, as is shown in FIG. 8, for this case an emergency stop switch 36 is also provided on the patient table 10 and/or external to this, with which the patient table 10 can be stopped in the event of an emergency.

Figure 9:
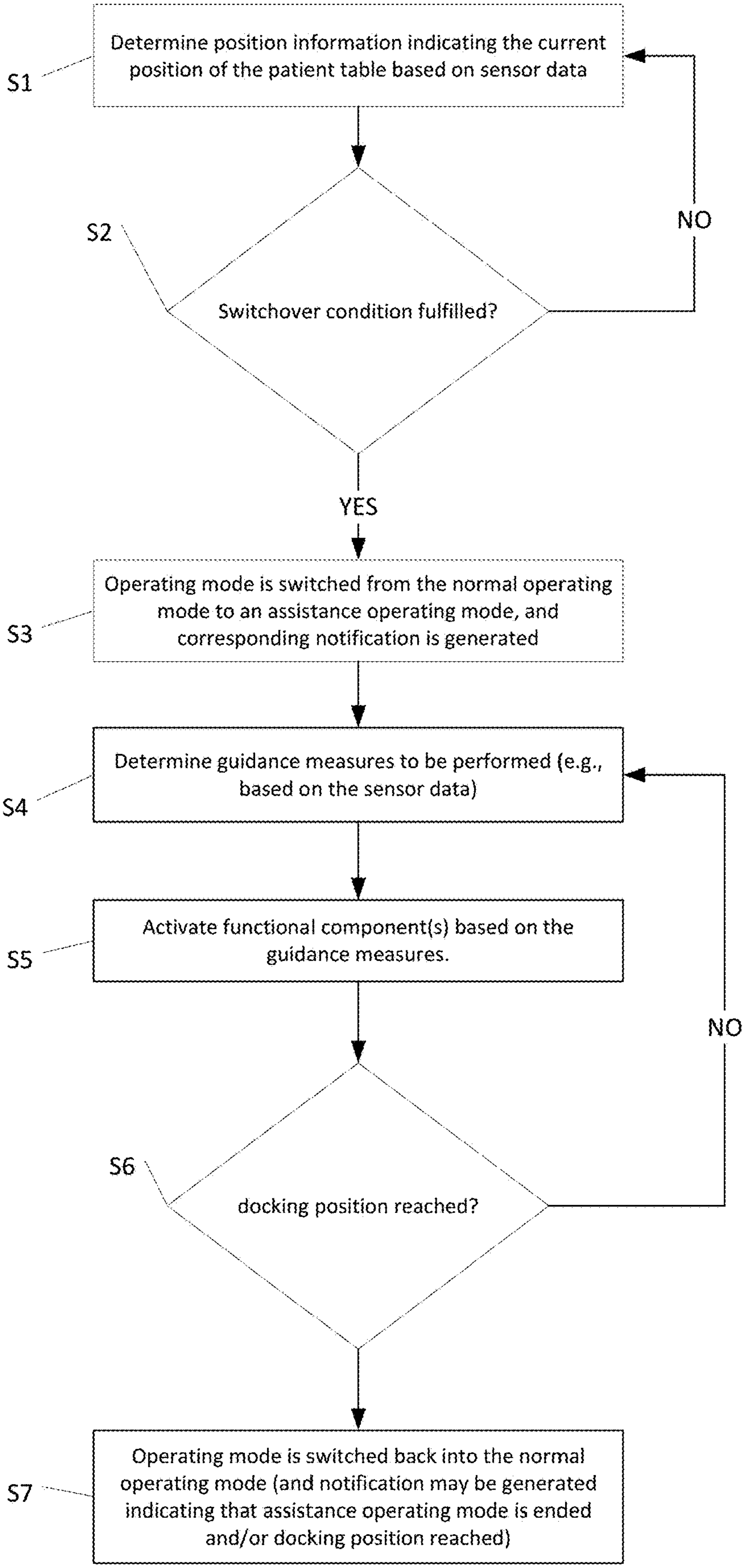
FIG. 9 is a flowchart of a method according to one or more exemplary embodiments of the disclosure.

For further clarification, FIG. 9 shows a general flowchart of the inventive method. In this figure, in a step S1 position information indicating the current position of the patient table 10 is determined from sensor data of the sensors of the sensor arrangement, in particular of the cameras 24, of the distance sensors 25 and of the magnetic field sensors 26.

This position information is used in step S2, also in respect of the direction of movement over time, in order to evaluate fulfillment of the switchover condition. If the switchover condition is fulfilled, the method continues with step S3, in which a switch is made from the normal operating mode into the assistance operating and the operator is notified of this by outputting the activation notification, in particular by means of the output means 23. The output means 23 may show a green light for the entire duration of the assistance operating mode.

Then, in step S4, guidance measures currently to be carried out are determined by the controller 18, in particular depending on group, as explained, on basis of the sensor data either by determination of the movement trajectory 27 or of the relative location trajectory line 29, in particular taking into consideration static and/or dynamic objects. Naturally the current position information is once again relevant here. Which guidance measures are precisely to be determined emerges depending on the exemplary embodiment, as described above (degrees of assistance of 1, 2, 3 or 4).

Then, in step S5, there is the activation of the functional components 19 in accordance with the guidance measures.

Then, in a step S6, a check is made as to whether the docking position 16 has been reached. If this is not the case, the method returns to step S4 in the next time step, where the guidance measures are updated on the basis of the current sensor data.

If the docking position is reached however, in step S7, where necessary only after the docking or the handover of the patient couch 8, a switch is made again back into the normal operating mode and in particular this ending of the assistance operating mode is also indicated.

Naturally a notification of conclusion can also be output explicitly by means of the output means 22, 23, which shows that the docking position 16 has been reached. Further, in step S7, a signal can also be given to the docking facility 5, which can immediately automatically continue with the docking, thus in particular establish the docking connection and draw in the patient couch 8. This can however also be enabled by a control element.

The various steps can be realized within the controller 18 by functional units. To this end, FIG. 10 shows a basic diagram of a possible functional layout of the controller 18. In this case, as well as a memory means 37, it initially has an evaluation unit (evaluator) 38 in order to evaluate the sensor data of the sensor arrangement for determination of the position information, cf. step S1. The evaluation unit (evaluator) 38 can also be used again in the steps S4 and S6.

The controller 18 further has a switchover unit (switchover controller) 39 for monitoring the switchover condition and for switching over when the switchover condition is fulfilled in accordance with step S2. The switchover unit 39 can also control the switch back into the normal operating mode.

Measure determination unit (guidance measurement) 40 adapted to determine guidance measures in accordance with step S4, which can then be implemented in an activation controller 41 accordingly by activation of the functional components 19.

Naturally further functional units can also be provided in order to carry out further steps in exemplary embodiments, or functional units can realize further tasks. In this way the switchover unit 39 or the activation unit 41 can also be embodied to activate the output means 22, 23 for output of the activation notification and/or the notification of conclusion.

Although the disclosure has been illustrated and described in greater detail by the exemplary embodiments, the disclosure is not restricted by the disclosed examples and other variations can be derived herefrom by the person skilled in the art, without departing from the scope of protection of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

The various components described herein may be referred to as "modules," "units," or "devices." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such modules, units, or devices, as applicable and relevant, may alternatively be referred to herein as "circuitry," "controllers," "processors," or "processing circuitry," or alternatively as noted herein.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for operation of a docking arrangement for establishing a docking position of a patient table necessary for docking, the docking arrangement having a docking facility for the patient table, a controller, and the patient table, the docking arrangement being connectable, by docking of the patient table at the docking facility, to a medical engineering facility associated with the docking facility, the method comprising:

determining, by the controller and based on sensor data, position information describing a position of the patient table, wherein determining the position information includes detecting, by a sensor arrangement of the docking arrangement, sensor data corresponding to: the position of the patient table relative to the docking arrangement, and/or to an environment feature describing a movement trajectory to the docking arrangement;

performing, by the controller and in response to a switchover condition indicative of a handover situation and a purely manual operation of the patient table by an operator, a switch into an assistance operating mode of the docking arrangement;

in the assistance operating mode, determining, by the controller and based on the sensor data, at least one guidance measure for the patient table adapted to establish the docking position by evaluating the sensor data, and activating and controlling a functional component of the patient table adapted to assist the operator; and determining by the controller, a steering intervention and/or longitudinal guidance intervention based on at least one comfort boundary condition related to comfort of a patient supported on the patient table;

wherein the comfort boundary condition comprises a maximum permitted curve radius.

2. The method as claimed in claim 1, wherein the handover situation comprises:

the position information indicating a position of the patient table in a handover area defined relative to the docking position.

3. The method as claimed in claim 1, wherein performing the switchover condition further comprises checking for fulfillment of at least one boundary condition including a current speed of the patient table being less than a speed threshold value.

4. The method as claimed in claim 3, further comprising generating a notification of non-fulfillment of the boundary condition, the notification being a visual and/or audible notification presented to the operator.

5. The method as claimed in claim 1, wherein the environment feature comprises a trajectory line provided on a floor and/or on a ceiling of the room in which the medical engineering facility is arranged.

6. The method as claimed in claim 1, wherein the switch into or out of the assistance operating mode is indicated to the operator by an optical, acoustic, and/or haptic notification output by at least one output interface of the patient table.

7. The method as claimed in claim 6, wherein output interface comprises at least one status light source extending longitudinally along at least one side of the patient table.

8. The method as claimed in claim 1, wherein at least one of the at least one guidance measures comprises an output of a guidance notification to the operator, wherein the functional component comprises an output interface adapted to generate an optical, acoustic, and/or haptic notification.

9. The method as claimed in claim 1, further comprising:

in response to a guidance measure describing a steering intervention, activating at least one steering actuator of the patient table adapted to implement the steering intervention as the functional component; and/or in response to a guidance measure describing a longitudinal guidance intervention, activating at least one longitudinal guidance actuator of the patient table adapted to implement the longitudinal guidance intervention as the functional component.

10. The method as claimed in claim 9, further comprising aborting the at least one guidance measure in response to an opposing action of the operator to the at least one guidance measure, wherein the at least one guidance measure corresponds to a steering intervention and/or a longitudinal guidance intervention.

11. The method as claimed in claim 9, further comprising evaluating, by the controller, handling data generated by a handling detector and/or a handling operating element provided on the patient table to determine handling information indicating monitoring and/or readiness for action by the operator, wherein the activation of the steering actuator and/or of the longitudinal guidance actuator occurs in response to the monitoring and/or readiness for action being indicated.

12. The method as claimed in claim 11, wherein the handling operating element comprises a dead man's handle adapted to be brought actively against a reset force into an actuation setting.

13. The method as claimed in claim 1, wherein the docking arrangement comprises an emergency stop switch, the controller being adapted to terminate the assistance operating mode in response to an actuation of the emergency stop switch.

14. The method as claimed in claim 1, wherein guidance measures exclusively related to the transverse guidance are determined and implemented.

15. The method as claimed in claim 1, wherein the medical engineering facility is a magnetic resonance facility.

16. The method as claimed in claim 15, wherein the sensor arrangement comprises at least one magnetic field sensor of the patient table, wherein the determination of the position information comprises reconciling the sensor data of the at least one magnetic field sensor with a magnetic field map of a stray field of the magnetic resonance facility in its environment.

17. A docking arrangement comprising:

a patient table having at least one functional component;

a docking facility adapted connect to a medical engineering facility in response to a docking of the patient table at the docking facility;

a sensor arrangement adapted to: (a) detect a position of the patient table relative to the docking arrangement, and/or detect an environment feature describing a movement trajectory to the docking arrangement; and (b) generate sensor data corresponding to the detected position and/or detected environment feature;

a controller adapted to:

determine, based on the sensor data, position information describing the position of the patient table;

control, in response to a switchover condition indicative of a handover situation and a purely manual operation of the patient table by an operator, the docking arrangement to switch into an assistance operating mode;

in the assistance operating mode, determine, based on the sensor data, at least one guidance measure for the patient table adapted to establish the docking position by evaluating the sensor data, and activating and controlling a functional component of the patient table adapted to assist the operator; and determine a steering intervention and/or longitudinal guidance intervention based on at least one comfort boundary condition related to comfort of a patient supported on the patient table;

wherein the comfort boundary condition comprises a maximum permitted curve radius.

* * * * *